United States Patent [19]
Stolle et al.

[11] Patent Number: 5,869,659
[45] Date of Patent: Feb. 9, 1999

[54] HETEROATOM-CONTAINING CYCLOPENTANOPYRIDYL-OXAZOLIDINONES

[75] Inventors: Andreas Stolle; Dieter Häbich; Bernd Riedl; Martin Ruppelt, all of Wuppertal; Stephen Bartel, Bergisch Gladbach; Walter Guarnieri, Zülpich, all of Germany; Hanno Wild, Orange, Conn.; Rainer Endermann; Hein-Peter Kroll, both of Wuppertal, Germany

[73] Assignee: Bayer Aktiengesellschaft, Leverkusen, Germany

[21] Appl. No.: 785,145

[22] Filed: Jan. 13, 1997

[30] Foreign Application Priority Data

Jan. 18, 1996 [DE] Germany .................. 19601627.4

[51] Int. Cl.⁶ .................. C07D 413/00; C07D 257/08; C07D 487/00; C07D 239/00
[52] U.S. Cl. .................. 544/114; 544/115; 544/118; 544/179; 544/184; 544/238; 544/254; 544/350
[58] Field of Search .................. 544/114, 115, 544/118, 179, 184, 238, 254, 350

[56] References Cited

U.S. PATENT DOCUMENTS

| | | | |
|---|---|---|---|
| 4,705,799 | 11/1987 | Gregory | 514/376 |
| 4,801,600 | 1/1989 | Wang et al. | 514/376 |
| 4,921,869 | 5/1990 | Wang et al. | 514/376 |
| 4,942,183 | 7/1990 | Gregory et al. | 514/376 |
| 4,965,268 | 10/1990 | Wang et al. | 514/253 |
| 4,985,429 | 1/1991 | Wang et al. | 514/253 |
| 5,164,510 | 11/1992 | Bricker | 548/231 |
| 5,254,577 | 10/1993 | Carlson et al. | 514/376 |
| 5,561,148 | 10/1996 | Gante et al. | 514/376 |
| 5,574,055 | 11/1996 | Borgulya et al. | 514/376 |
| 5,627,181 | 5/1997 | Riedl et al. | 514/236.8 |

FOREIGN PATENT DOCUMENTS

| | | |
|---|---|---|
| 0 405 976 A1 | 1/1991 | European Pat. Off. . |
| 405976 | 1/1991 | European Pat. Off. . |
| 0 609 441 A1 | 8/1994 | European Pat. Off. . |
| 0 609 905 A1 | 8/1994 | European Pat. Off. . |
| 0 657 440 A1 | 6/1995 | European Pat. Off. . |
| WO 93/08179 | 4/1993 | WIPO . |

OTHER PUBLICATIONS

C. Park et al., J.Med.Chem., vol. 35, pp. 1156–1165 (1992).
K. Rüfenacht, Helv.Chem.Acta, vol. 59, pp. 1593–1612 (1976).
C. Okafor, J.Org.Chem., vol. 38, No. 26, pp. 4383–4386 (1973).
J. Swenson et al., Antimicrobial Agents and Chemotheraphy, vol. 22, No. 2, pp. 186–192 (1982).

*Primary Examiner*—Mukund J. Shah
*Assistant Examiner*—Tamthom T. Ngo
*Attorney, Agent, or Firm*—Sprung Kramer Schaefer & Briscoe

[57] ABSTRACT

The present invention relates to heteroatom-containing cyclopentanopyridyl-oxazolidinones, processes for their preparation and their use as medicaments, in particular as antibacterial medicaments.

8 Claims, No Drawings

HETEROATOM-CONTAINING CYCLOPENTANOPYRIDYL-OXAZOLIDINONES

The present invention relates to heteroatom-containing cyclopentanopyridyl-oxazolidinones, processes for their preparation and their use as medicaments, in particular as antibacterial medicaments.

3-(Nitrogen-substituted)phenyl-5-beta-amidomethyloxazolidin-2-ones having antibacterial action are disclosed in EP 609 905.

Furthermore, oxazolidinone derivatives having a monoaminoxidase inhibitory action are published in WO 93 08 179 A and EP 657 440 and oxazolidinone derivatives having action as adhesion receptor antagonists are published in EP 645 376.

The present invention relates to heteroatom-containing cyclopentanopyridyl-oxazolidinones of the general formula (I)

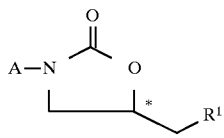

in which

A represents a radical of the formula

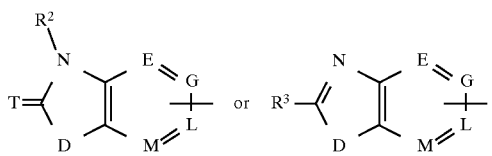

in which
  E, G, L and M are identical or different and at least one of these substituents denotes a nitrogen atom and the others denote the radical of the formula —CR$^4$,
  in which
    R$^4$ represents hydrogen, methyl or halogen,
  R$^2$ represents hydrogen, cycloalkyl or cycloalkylcarbonyl each having 3 to 8 carbon atoms, or straight-chain or branched alkyl having up to 8 carbon atoms, which is optionally substituted by hydroxyl, halogen, by straight-chain or branched alkoxy, alkoxycarbonyl or alkythio each having up to 6 carbon atoms or by a radical of the formula —NR$^6$R$^7$,
  in which
    R$^6$ and R$^7$ are identical or different and denote hydrogen, cycloalkyl, phenyl or straight-chain or branched alkyl having up to 4 carbon atoms,
  R$^3$ denotes straight-chain or branched alkyl or thioalkyl each having up to 8 carbon atoms,
  D denotes an oxygen or sulphur atom or a group of the formula

—NR$^5$, in which
    R$^5$ has the meaning of R$^2$ indicated above and is identical to or different form this,
  T denotes an oxygen or sulphur atom,
  R$^1$ represents azido, hydroxyl or a group of the formula —OR$^8$, O—SO$_2$R$^9$ or —NR$^{10}$R$^{11}$,
  in which
    R$^8$ denotes straight-chain or branched acyl having up to 8 carbon atoms or hydroxyl protective group,
    R$^9$ denotes straight-chain or branched alkyl having up to 4 carbon atoms or phenyl which is optionally substituted by straight-chain or branched alkyl having up to 4 carbon atoms,
    R$^{10}$ and R$^{11}$ are identical or different and denote cycloalkyl having 3 to 6 carbon atoms, hydrogen, phenyl or straight-chain or branched alkyl or alkoxy each having up to 8 carbon atoms or an amino protective group,
    or
    R$^{10}$ or R$^{11}$ denotes a group of the formula —CO—R$^{12}$, —CS—R$^{12'}$, P(O)(OR$^{13}$)(OR$^{14}$) or —SO$_2$R$^{15}$,
    in which
      R$^{12}$ and R$^{12'}$ are identical or different and denote hydrogen, cycloalkyl having 3 to 6 carbon atoms, trifluoromethyl, straight-chain or branched alkoxy having up to 8 carbon atoms, phenyl, benzyloxy or hydrogen, or
      denote straight-chain or branched alkyl having up to 8 carbon atoms, which is optionally substituted by cyano, halogen or trifluoromethyl,
      or
      denote straight-chain or branched thioalkyl or acyl each having up to 6 carbon atoms,
      or
      denote a group of the formula —NR$^{16}$R$^{17}$,
      in which
        R$^{16}$ and R$^{17}$ are identical or different and denote hydrogen, phenyl or straight-chain or branched alkyl having up to 6 carbon atoms,
        or
        denote a 5-membered aromatic heterocycle having up to 3 heteroatoms from the series S, N, and/or O,
      R$^{13}$ and R$^{14}$ are identical or different and denote hydrogen or straight-chain or branched alkyl having up to 4 carbon atoms,
      R$^{15}$ denotes straight-chain or branched alkyl having up to 4 carbon atoms or phenyl,
and their salts.

Physiologically acceptable salts of the heteroatom-containing cyclopentanopyridyl-oxazolidinones can be salts of the substances according to the invention with mineral acids, carboxylic acids or sulphonic acids. Particularly preferred salts are, for example, those with hydrochloric acid hydrobromic acid, sulphuric acid, phosphoric acid, methansulphonic acid, ethanesulphonic acid, toluensulphonic acid, benzenesulphonic acid, naphthalenedisulphonic acid, acetic acid propionic acid, lactic acid, tartaric acid, citric acid, fumaric acid, maleic acid, benzoic acid.

Salts which may be mentioned are salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

Reaction products with $C_1$–$C_4$-alkyl halides, in particular $C_1$–$C_4$-alkyl iodides, can additionally function as salts.

Heterocycle in general represents a 5- to 6-membered, saturated or unsaturated ring which as heteroatoms can contain up to 3 oxygen, sulphur and/or nitrogen atoms. The following are preferred: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

Hydroxyl protective group in the context of the definition given above in general represents a protective group from the series: trimethylsilyl, triisopropylsilyl, tert-butyldimethylsilyl, benzyl, benzyloxycarbonyl, 2-nitrobenzyl, 4-nitrobenzyl, tert-butoxycarbonyl, allyloxycarbonyl, 4-methoxybenzyl, 4-methoxybenzyloxycarbonyl, tetrahydropyranyl, formyl, acetyl, trichloroacetyl, 2,2,2-trichlorethoxycarbonyl, methoxyethoxymethyl, [2-(trimethylsiyl)ethoxy]methyl, benzoyl, 4-methylbenzoyl,4-nitrobenzoyl, 4-fluorobenzoyl, 4-chlorobenzyl or 4-methoxybenzoyl. Acetyl, tert-butyldimethylsilyl or tetrahydropyranyl are preferred.

Amino protective groups in the context of the invention are the customary amino protective groups used in peptide chemistry.

These preferably include: benzyloxycarbonyl, 2,4-dimethyloxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 2,2,2-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl.

The compounds according to the invention can exist in stereoisomeric forms which behave either as image and mirror image (enantiomers), or which do not behave as image and mirror image (diastereomers). The invention relates both to the enantiomers or diastereomers and their respective mixtures. Like the diastereomers, the racemic forms can be separated into the sterisomerically uniform constituents in a known manner.

Preferred compounds of the general formula (I) are those in which

A represents a radical of the formula

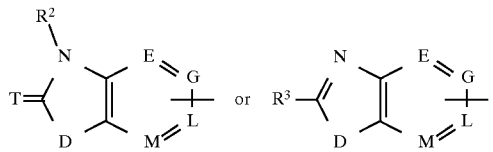

in which

E, G, L and M are identical or different and at least one of the substituents denotes a nitrogen atom and the others denote the radical of the formula —$CR^4$, in which $R^4$ denotes hydrogen, fluorine, chlorine or bromine, $R^2$ denotes hydrogen, cyclopropyl, cyclobutyl, cyclopentyl, cyclohexyl or cycloheptyl, or denotes straight-chain or branched alkyl having up to 6 carbon atoms, which is optionally substituted by hydroxyl, fluorine, chlorine, bromine, by straight-chain or branched alkoxy, alkoxycarbonyl or alkothio each having up to 4 carbon atoms or by a radical of the formula —$NR^6R^7$, in which $R^6$ and $R^7$ are identical or different and denote hydrogen, cyclopropyl, cyclobutyl, cyclopentyl, cyclohexyl, phenyl or straight-chain or branched alkyl having up to 3 carbon atoms, $R^3$ denotes straight-chain or branched alkyl or thioalkyl each having up to 6 carbon atoms, D denotes an oxygen or sulphur atom or a group of the formula —$NR^5$, in which $R^5$ has the meaning of $R^2$ indicated above and is identical to or different from this, T denotes an oxygen or sulphur atom, $R^1$ represents azidio, hydroxyl or a group of the formula —$OR^8$, O—$SO_2R^9$ or —$NR^{10}R^{11}$, in which $R^8$ denotes straight-chain or branched acyl having up to 6 carbon atoms or benzyl, $R^9$ denotes straight-chain or branched alkyl having up to 3 carbon atoms, phenyl or tolyl, $R^{10}$ and $R^{11}$ are identical or different and denote cyclopropyl, cyclopentyl, cyclohexyl, hydrogen, phenyl or straight-chain or branched alkyl or alkoxy each having up to 6 carbon atoms, tert-butoxycarbonyl or benzyloxycarbonyl, or $R^{10}$ or $R^{11}$ denotes a group of the formula —CO—$R^{12}$, —CS—$R^{12'}$, P(O)($OR^{13}$)($OR^{14}$) or —$SO_2$—$R^{15}$, in which $R^{12}$ and $R^{12'}$ are identical or different and denote hydrogen, cyclopropyl, cyclobutyl, cyclopentyl, cyclohexyl, trifluoromethyl or straight-chain or branched alkoxyl having up to 6 carbon atoms, phenyl, benzyloxy or hydrogen, or denote straight-chain or branched alkyl having up to 6 carbon atoms, which is optionally substituted by cyano, fluorine, chlorine, bromine or trifluoromethyl, or denote straight-chain or branched thioalkyl of acyl each having up to 5 carbon atoms, or denote a group of the formula —$NR^{16}R^{17}$, in which $R^{16}$ and $R^{17}$ are identical or different and denote hydrogen, phenyl or straight-chain or branched alkyl having up to 4 carbon atoms, or denote isoazolyl, furyl, thienyl, pyrryl, oxazolyl or imidazolyl, $R^{13}$ and $R^{14}$ are identical or different and denote hydrogen or straight-chain or branched alkyl having up to 3 carbon atoms, $R^{15}$ denotes straight-chain or branched alkyl having up to 3 carbon atoms or phenyl, and their salts.

Particularly preferred compounds of the general formula (I) are those
in which

A represents a radical of the formula

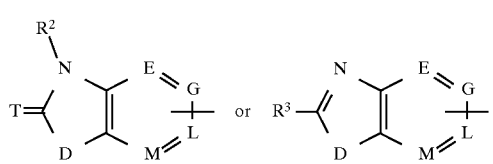

in which

E, G, L and M are identical or different and at least one of the substituents denotes a nitrogen atom and the others denote the radical of the formula —$CR^4$, in which $R^4$ denotes hydrogen or fluorine, $R^2$ denotes hydrogen, cyclopropyl, cyclobutyl, cyclopentyl or cyclohexyl, or denotes straight-chain or branched alkyl having up to 5 carbon atoms, which is optionally substituted by hydroxyl, fluorine, chlorine, bromine, by straight-chain or branched alkoxy, alkoxycarbonyl or alkythio each having up to 3 carbon atoms or by a radical of the formula —NR⁶R⁷, in which
$R^6$ and $R^7$ are identical or different and denote hydrogen, cyclopropyl, cyclopentyl, cyclohexyl, phenyl, or straight-chain or branched alkyl having up to 3 carbon atoms.

$R^3$ denotes straight-chain or branched alkyl or thioalkyl each having up to 5 carbon atoms, D denotes an oxygen or sulphur atom, T denotes an oxygen atom, $R^1$ represents azido, hydroxyl or a group of the formula —$OR^8$, O—$SO_2R^9$ or —$NR^{10}R^{11}$, in which
$R^8$ denotes straight-chain or branched acyl having up to 5 carbon atoms or benzyl, $R^9$ denotes methyl, ethyl, phenyl or tolyl, $R^{10}$ and $R^{11}$ are identical or different and denote cyclopropyl, cyclopentyl, cyclohexyl, hydrogen, phenyl or straight-chain or branched alkyl or alkoxy each having up to 5 carbon atoms, tert-butoxycarbonyl or benzyloxycarbonyl, or $R^{10}$ or $R^{11}$ denotes a group of the formula —CO—$R^{12}$, —CS—$R^{12'}$, P(O)(OR$^{13}$)(OR$^{14}$) or —$SO_2$—$R^{15}$, in which
$R^{12}$ and $R^{12'}$ are identical or different and denote hydrogen, cyclopropyl, cyclobutyl, cyclopentyl, trifluoromethyl or straight-chain or branched alkoxy having up to 5 carbon atoms, phenyl, benzyloxyl or hydrogen, denote straight-chain or branched alkyl having up to 5 carbon atoms, which is optionally substituted by cyano, fluorine, chlorine, bromine, or trifluoromethyl, or denote straight-chain or branched thioalkyl or acyl each having up to 4 carbon atoms, or denote a group of the formula —$NR^{16}R^{17}$, in which
$R^{16}$ and $R^{17}$ are identical or different and denote hydrogen, phenyl or straight-chain or branched alkyl having up to 3 carbon atoms, or denote isoazolyl, furyl, oxazolyl or imidazolyl, $R^{13}$ and $R^{14}$ are identical or different and denote hydrogen, methyl or ethyl, $R^{15}$ denotes methyl or phenyl and their salts.

Very particularly preferred compounds of the general formula (I) are those
in which
the oxazolidinone radical bonded to the nitrogen-containing ring in position 5 or 6.

Processes for the preparation of the compounds of the general formula (I) according to the invention have additionally been found, characterized in that

[A] compounds of the general formula (II) or (III)

   (II)

or

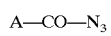   (III)

in which

A has the meanings indicated above,
are reacted with lithium bromide/$(C_4H_9)_3P(O)$ and epoxides of the general formula (IV)

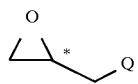   (IV)

in which
Q represents $C_1$–$C_6$-acyloxy,
in inert solvents, if appropriate in the presence of a base, and if $R^1$=OH, the hydroxyl function is liberated by a typical ester hydrolysis or by a typical transesterification,

[B] compounds of the general formula (V)

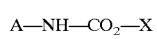   (V)

in which
A has the meaning indicated above
and
X represents a typical protective group, preferably benzyl, are reacted in inert solvents and in the presence of a base, for example lithium alkyls or lithium N-alkyl- or lithium N-silylalkylamides, preferably n-butyllithium, with epoxides of the general formula (IV), or

[C] if $R^1$=OH, compounds of the general formula (III) are first converted by elimination of nitrogen in alcohols into the compounds of the general formula (Va)

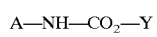   (Va)

in which
A has the meaning indicated above
and
Y represents straight-chain or branched $C_1$–$C_6$-alkyl, preferably n-butyl, and these are reacted in a second step as described under [A] with epoxides of the general formula (IV) in inert solvents and in the presence of a base, preferably lithium N-alkyl- or N-Silylalkylamides or n-butyllithium, or

[D] compounds of the general formula (V) are first converted by reaction with allyl bromide in inert solvents and in the presence of a base into the compounds of the general formula (VI)

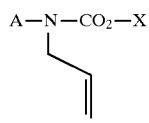   (VI)

in which
A and X have the meaning indicated above,
then using osmium tetroxide/N-methylmorpholine N-oxide the compounds of the general formula (VII)

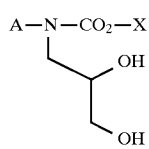   (VII)

in which
A and X have the meaning indicated above,
are prepared and in a last step a cyclization is carried out using bases in acetonitrile, preferably using potassium carbonate, or
[E] compounds of the general formula (VIII).

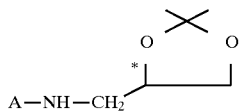 (VIII)

in which
A has the meaning indicated above,
are either reacted directly with acids and diethyl carbonate,
or first by reaction of the compounds of the general formula (VIII) with acids the compounds of the general formula (IX)

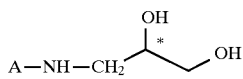 (IX)

in which
A has the meaning indicated above,
are prepared,
and these are then cyclized in the presence of an auxiliary and/or an acid in inert solvents,
or
[F] first the heterocycle amines (A—NH$_2$) are reacted with a compound of the general formula (IV) to give a compound of the general formula (IX) and this is then cyclized with carbonyldiimidazole/methylene chloride, (Et$_2$)$_2$CO or phosgene, diphosgene or triphosgene as described under [E],
or
[G] first compounds of the general formula (Ia)

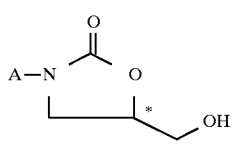 (Ia)

in which
A has the meaning indicated above,
are converted by reaction with (C$_1$-C$_4$)-alkyl- or phenylsulphonyl chlorides in inert solvents and in the presence of a base into the corresponding compounds of the general formula (Ib)

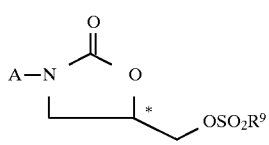 (Ib)

in which
A and R$^9$ have the meaning indicated above, then using sodium azide in inert solvents the azides of the general formula (Ic)

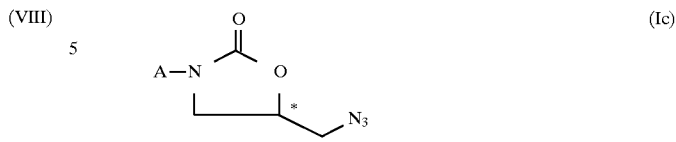 (Ic)

in which
A has the meaning indicated above,
are prepared,
these are converted in a further step by reaction with (C$_1$-C$_4$—O)$_3$-P or PPh$_3$, preferably (CH$_3$O)$_3$P in inert solvents and with acids into the amines of the general formula (Id)

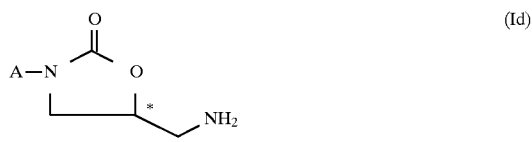 (Id)

in which
a has the meaning indicated above,
and by reaction with acetic anhydride or other acylating agents of the general formula (X)

 (X)

R$^{18}$—CO—R$^{12}$ in which
R$^{12}$ has the meaning indicated above
and
R$^{18}$ represent halogen, preferably chlorine or the radical —OCOR$^{12}$,
in inert solvents the compounds of the general formula (Ie)

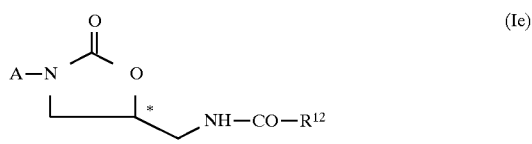 (Ie)

in which
A and R$^{12}$ have the meaning indicated above,
are prepared,
and if R$^1$=NR$^{10}$—CSR$^{12}$ compounds of the general formula (Id) are reacted with ethyl dithiocarboxylates and triethylamine and, if R$^1$=NR$^{12}$—CS—NR$^{16}$R$^{17}$, with thioisocyanates.

The processes according to the invention can be illustrated by way of example by the following reaction schemes:

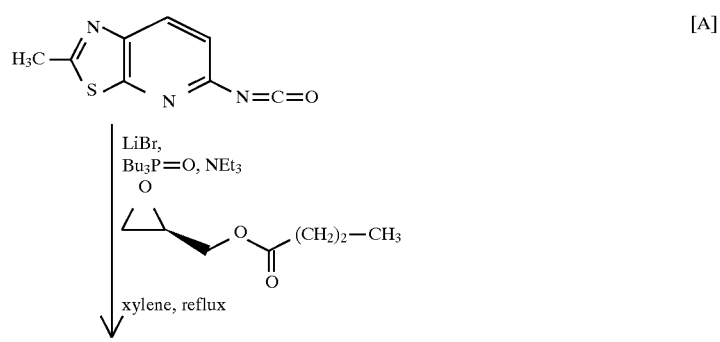 [A]

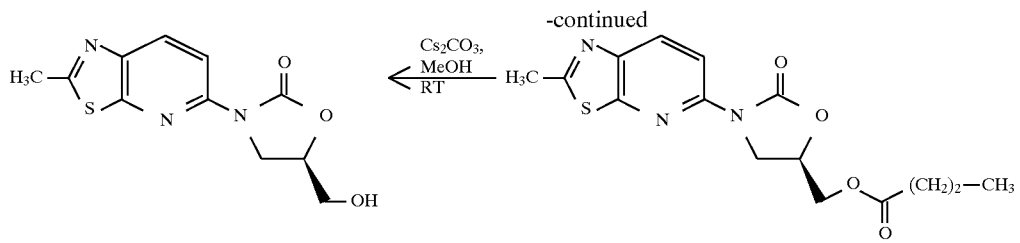
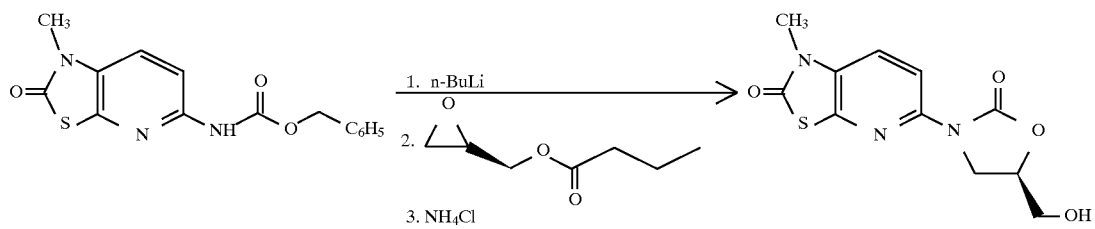
[B]
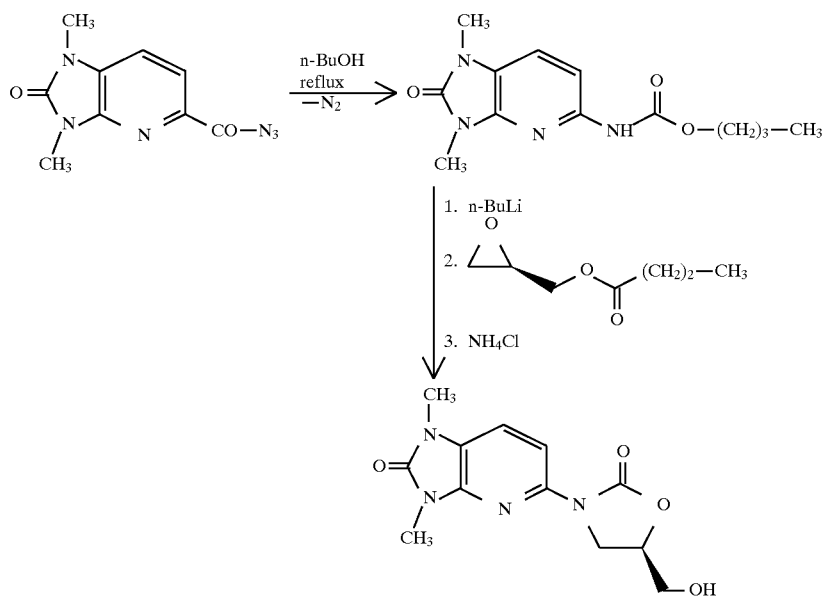
[C]
[D]
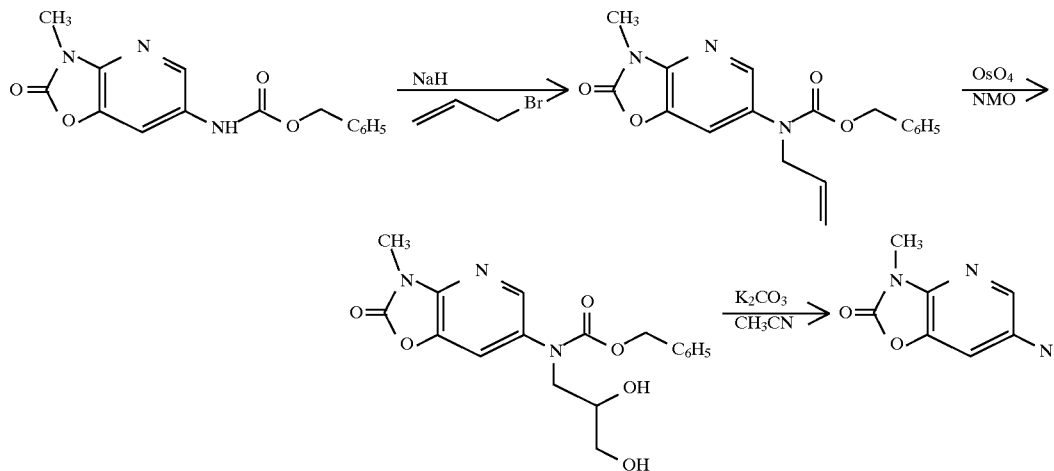
[E]
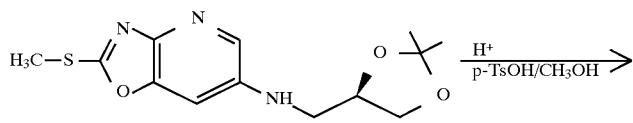

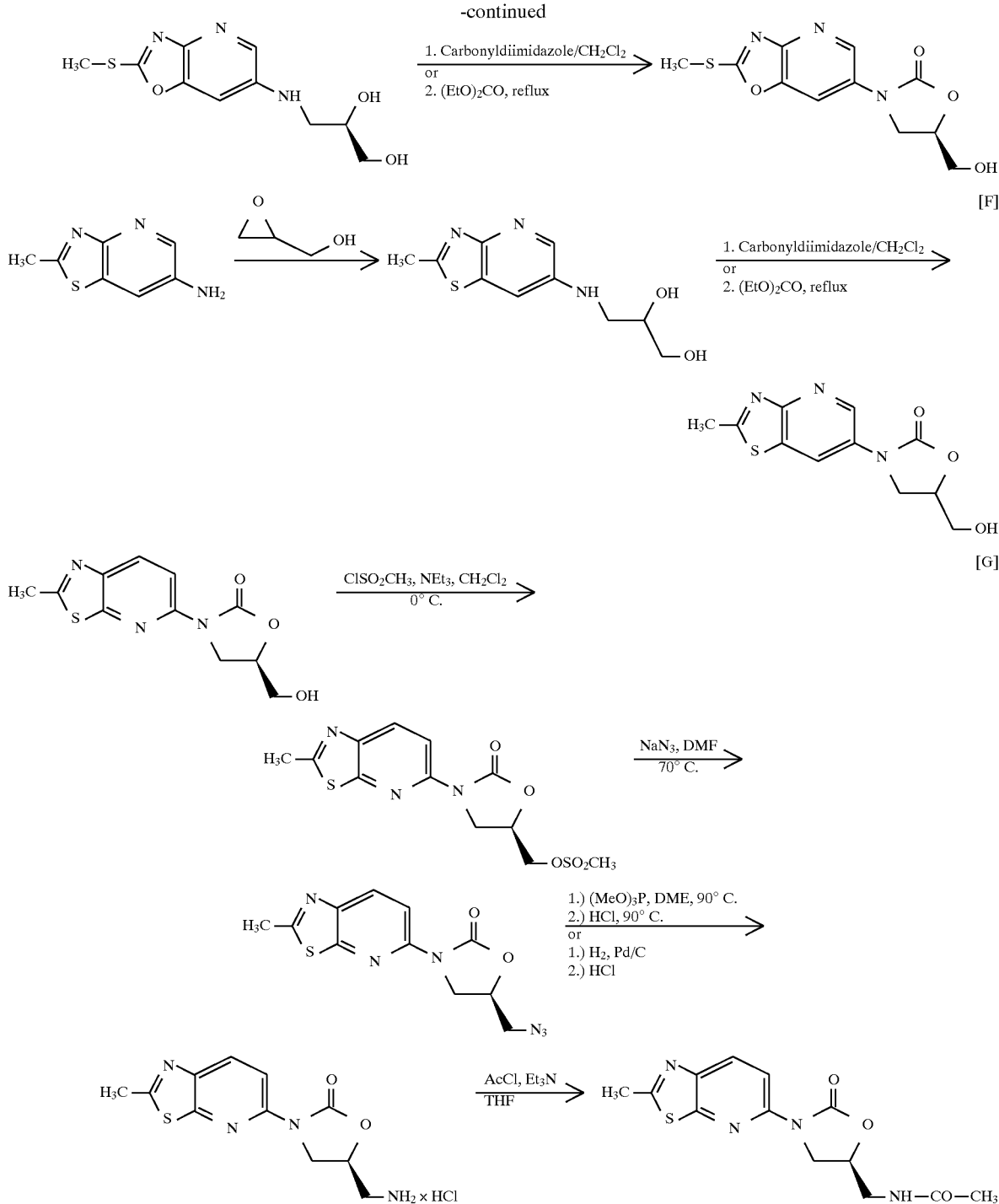

Suitable solvents, depending on the individual process steps, are the customary solvents which do not change under reaction conditions. These preferably include alcohols such as methanol, ethanol, proponal or isopropanol, of ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethylphosphoramide, or hydrocarbons such as hexane, benzene, dichlorobenzene, xylene or toluene, or dimethyl sulphoxide, acetnitrile, ethyl acetate, or halogenohydrocarbons such as methylene chloride, chloroform or carbon tetrachloride, or pyridine, picoline or N-methylpiperidine. Mixtures of the solvents mentioned can also be used.

Suitable bases, depending of the individual process steps, are the customary inorganic or organic bases. These preferably includes alkali metal hydroxides such as, for example, sodium or potassium hydroxide, or alkali metal carbonates such as sodium or potassium carbonate, or alkali metal alkoxides such as, for example sodium or potassium methoxide or sodium or potassium ethoxide, or organic amines such as ethyldiisopropylamine, triethylamine, picoline, pyridines or N-methylpiperidine, or amides such as sodium amide or lithium diisopropylamide, or lithium N-silylalkylamides, such as, for example, lithium N-(bis)triphenylsilylamide or lithium alkyls such as n-butyllithium.

the base is employed in an amount of from 1 mol to 10 mol, preferably from 1 mol to 3 mol, relative to 1 mol of the compounds of the general formulae (II), (III), (IV) and (Va).

All reaction are in general carried out at normal, elevated or at reduced pressure (e.g. 0.5 to 5 bar). The reaction is in general carried out at normal pressure.

Process [A] is preferably carried out in xylene or dichlorobenzene, if appropriate in the presence of triethylamine, under reflux.

The base-catalysed transesterification is carried out using one of the abovementioned alcohols, preferably methanol, in a temperature range from −10° C. to +40° C., preferably at room temperature.

Suitable bases are in general hydrogen carbonate, sodium methoxide, hydrazine hydrate, potassium carbonate or caesium carbonate. Caesium carbonate is preferred.

Process [B] is carried out in one of the abovementioned ethers using lithium alkyl compounds or lithium N-silylamides, such as, for example, n-butyllithium, lithium diisopropylamide or lithium bistrimethylsilylamide, preferably in tetrahydrofuran and lithium bis-trimethylsilylamide or n-butyllithium, in temperature range from −100° C. to +20° C., preferably from −75° C. to −40° C.

For process [C], preferably the abovementioned alcohols, in the case of subsequent cyclization tetrahydrofuran, are suitable for the 1st step.

Suitable bases for the cyclization are preferably the abovementioned lithium N-silylalkyl compounds or n-butyllithium, n-Butyllithium is particularly preferred.

The first reaction step is carried out at the boiling point of the appropriate alcohol and the cyclization is carried out in a temperature range from −70° C. to room temperature.

Suitable bases for the 1st step of process [D] are in general lithium alkyls, lithium N-alkyls or alkali metal hydrides such as, for example, butyllithium or sodium hydride. Sodium hydride is preferred.

The base is in general employed in an amount of from 1 mol to 5 mol, preferably 1 mol to 1.5 mol, relative to 1 mol of the compound of the general formula (VI).

The cyclization is carried out in one of the abovementioned solvents and bases, potassium carbonate and acetonitrile being preferred.

The base is employed in an amount of from 1 mol to 10 mol, preferably from 1 mol to 3 mol, relative to 1 mol of the compounds of the general formulae (II), (III), (IV) and (Va).

All reaction are in general carried out at normal, elevated or at reduced pressure (e.g. 0.5 to 5 bar). In general, the reactions are carried out at normal pressure.

The reaction steps are in general carried out in a temperature range from −78° C. to 100° C., preferably from −20° C. to 50° C.

The cyclization [E] is carried out in the presence of an auxiliary and/or the presence of an acid.

Suitable acids are in the general inorganic acids such as, for example, hydrochloric acid or sulphuric acid, or organic carboxylic acids having 1–6 C atoms, if appropriate substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acids, ethanesulphonic acid, benzenesulphonic acid or toluenesulphonic acid, hydrochloric acid is particularly preferred.

The acid is employed in an amount of from 1 mol to 10 mol, preferably from 1 mol to 2 mol, relative to 1 mol of the compounds of the general formula (VII).

Suitable auxiliaries are the customary reagents such as phosgene, carbonyldiimidazole or diethyl carbonate or trichloromethyl chloroformate. Carbonyldiimidazole, diethyl carbonate and trichloromethyl chloroformate are preferred.

Suitable solvents are the abovementioned halogenohydrocarbons. Methylene chloride is preferred.

The cyclizations are in general carried out in a temperature range from −20° C. to 100° C., preferably at −20° C. to room temperature.

Process [F] is carried out in analogy to the conditions mentioned under [E].

The acylation [G] is in general carried out in one of the abovementioned ethers or halogenohydrocarbons, preferably tetrahydrofurnal or methylene chloride, in a temperature range from −30° C. to 50° C., preferably from −10° C. to room temperature.

The reductions are in general carried out using hydrides in inert solvents or using boranes, diboranes or complex compounds thereof.

The reduction can in general be carried out by means of hydrogen in water or in inert organic solvents such as alcohols, ethers or halogenohydrocarbons, or mixtures thereof, using catalysts such as Raney nickel, palladium, palladium on animal carbon or platinum, or using hydrides or boranes in inert solvents, if appropriate in the presence of a catalyst.

Preferably, the reductions are carried out using hydrides, such as complete borohydrides or aluminum hydrides, as well as boranes. Sodium borohydride, lithium borohydride, sodium cyanoborohydride, lithium aluminum hydride, sodium bis-(2-methoxyethoxy)aluminum hydride or borane-tetrahydrofuran are particularly preferably employed here.

The reduction of hydrogeneration of the azides [G] is carried out using $(CH_3O)_3P$ and hydrochloric acid.

The reduction is in general carried out in a temperature range from −50° C. to the respective boiling point of the solvent, preferably from −20° C. to +90° C.

Suitable solvents in this context are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoramide or dimethylformamide, or acetic acid. It is also possible to use mixtures of the solvents mentioned.

The hydroxyl protective groups are in general removed according to a customary method, for example by hydrogenolytic cleavage of the benzyl ethers in the above mentioned inert solvents in the presence of a catalyst using hydrogen gas.

The amino protective group is in general also removed by customary methods, to be specific preferably Boc using hydrochloric acid in dioxane, Fmoc using piperidine and Z using HBr/HOAc or by hydrogenolysis.

Preferred derivatization reactions are redox reactions, reductive amination, transesterification and the halogenation of methyl groups using N-bromosuccinimide (NBS) or N-chlorosuccinimide (NCS), which are illustrated by way of example in the following.

Suitable solvents for the alkylation are customary organic solvents which do not change under the reaction conditions. These preferably include ethers such as diethyl ether, dioxane, tetrahydrofuran, glycol dimethyl ether, or hydrocarbons such as benzene, tolune, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, acetonitrile, acetone or nitromethane. It is also possible to use mixtures of the solvents mentioned. Dichloromethane, dimethyl sulphoxide and dimethylformamide are preferred.

The alkylation is carried out in the abovementioned solvents at temperatures of from 0° C. to +150° C., preferably at room temperature to +100° C., at normal pressure.

The amidation and the sulphoamidation are in general carried out in inert solvents in the presence of a base and of dehydrating agent.

Suitable solvents in this context are inert organic solvents which do not change under the reaction conditions. These include halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetonitrile or tetrahydrofuran. It is also possible to employ mixtures of the solvents. Dichloromethane and tetrahydrofuran are particularly preferred.

Suitable bases for the amidation and the sulphoamidation are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alkoxides such as, for example, sodium methoxide or ethoxide, potassium methoxide or ethoxide or potassium tert-butoxide, or organic amines such as benzyltrimethylammonium hydroxide, tetrabutylammonium hydroxide, pyridine, triethylamine or N-methylpiperidine.

The amidation and the sulphoamidation are in general carried out in a temperature range from 0° C. to 150° C., preferably at 25° C. to 40° C.

The amidation and the sulphoamidation are in general carried out at normal pressure. However, it is also possible to carry out the process at reduced pressure or at elevated pressure (e.g. in a range from 0.5 to 5 bar).

When carrying out the amidation and the sulphoamidation, the base is in general employed in an amount of from 1 to 3 mol, preferably from 1 to 1.5 mol, relative to 1 mol of the respective carboxylic acid.

Suitable dehydrating reagents are carboniimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-2-sulphonate or propanephosphonic anhydride or isobutyl chloroformate or benzotriazoyloxy-tris-(dimethylamino)phosphonium hexafluorophosphate diphenyl phosphoramidate or methanesulphonyl chloride, if appropriate in the presence of bases such as triethylamine or N-ethylmorpholine or N-methylpiperidine or 4-dimethylaminopyridine.

Suitable bases for the hydrolysis are the customary inorganic bases. These preferably included alkali metal hydroxides or alkaline earth metal hydroxides such as, for example sodium hydroxide, potassium hydroxide or barium hydroxide, or alkali metal carbonates such as sodium or potassium carbonate or sodium hydrogen carbonate. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol and isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

When carrying out the hydrolysis, the base is in general employed in an amount of from 1 to 3 mol, preferably from 1 to 1.5 mol, relative to 1 mol of the ester. Molar amounts of the reactants are particularly preferably used.

The esterification is in general carried out using the appropriate alcohols in the presence of acids, preferably sulphuric acid, in a temperature range from 0° C. to 150° C., preferably from 50° C. to 100° C., and at normal pressure.

The compounds of the general formulae (IV) and (X) are known or can be prepared by customary methods.

The compounds of the general formula (IX) are in the main new and can be prepared, for example, as described above.

The compounds of the general formula (II) are known in some cases or are new and can then be prepared, for example, by reacting the appropriate amines with trichloroethyl chloroformate in one of the abovementioned solvents, preferably xylene at reflux temperature.

The compounds of the general formula (III) are known in some cases or are new and can then be prepared, for example, by reacting, starting from the appropriate carboxylic acids, either with isobutyl chloroformate/acetone, sodium azide/water or with diphenylphosphoryl azide/tetrahydrofuran or with xylene or methylene chloride in the presence of one of the bases indicated above, preferably triethylamine, at –10° C. to room temperature.

The compounds of the general formulae (V) and (Va) are known in some cases or are new and can then be prepared either by elimination of nitrogen from the corresponding carbonyl azides and reaction with appropriate alcohols or by reaction of the corresponding amides with chloroformic acid esters, preferably benzyl chlorformate in one of the abovementioned solvents, preferably tetrahydrofuran or dioxane, in a temperature range from –10° C. to 200° C., preferably from 0°0 C. to 150° C.

The compounds of the general formulae (VI) and (VII) can be prepared by the abovementioned methods.

The compounds of the general formula, (Ia) are new and can be prepared, for example, as described under [A], [B], [C], [D], [E] or [F].

The compounds of the general formula (Ib), (Ic), (Id) and (Ie) are new and can be prepared as described above.

The compounds of the general formula (VIII) are in the main known or are new and can be prepared, for example, by reacting starting from the free amines (Ia), either with the acetonide of glycer aldehyde in methanol and in the presence of sodium acetate/sodium cyanoborohydride or of sodium borohydride and methanol in a temperature range from –20° C. to +40° C., preferably from –10° C. to 20° C., and at normal pressure.

The minimum inhibitory concentrations (MICs) were determined by serial dilution tests on Iso-Sensitest agar (Oxoid). For each test substance, a number of agar plates were prepared which contained decreasing concentrations of the active compound. The agar plates were inoculates using a multipoint inoculator (Denley). For inoculation, overnight cultures of the pathogenic organisms were used which had previously been diluted such that each inoculation point contained about $10^4$ colony-forming particles. The inoculated agar plates were incubated at 37° C., and the microorganism growth was read off after about 20 hours. The MICs (µg/ml) indicates the lowest active compound concentration at which no growth could be detected using the naked eye.

| | | | MICs (µg/ml): | | | | |
|---|---|---|---|---|---|---|---|
| Ex. No. | Staph. 133 | Staph. 48N | Staph. 25701 | Staph. 9TV | E. coli Neumann | Klebs. 57 USA | Psdm. Bonn |
| 10 | 8 | 8 | 8 | 4 | >64 | >64 | >64 |
| 11 | 8 | 8 | 8 | 4 | >64 | >64 | >64 |
| 12 | 8 | 8 | 8 | 4 | >64 | >64 | >64 |
| 13 | 8 | 8 | 8 | 4 | >64 | >64 | >64 |
| 14 | 4 | 8 | 4 | 2 | >64 | >64 | >64 |

For rapidly growing mycobacteria, the MIC determination was carried out following the method of broth microdilution described by Swenson [cf. J. M. Swenson, C. Thornberry, U. A. Silcox, Rapidly growing mycobacteria. Testing of suceptibility to 34 antimicrobial agents by broth microdilution. Antimicrobial Agents and Chemotherapy Vol. 22, 186–192 (1982)]. A deviation from this was the brain-heart extract medium treated with 0.1% by volume of Tween 80.

The mycobacterial strains used were obtained from the DSM (German Collection of Microorganisms, Braunschweig). They were incubated at 37° C. in a humid chamber.

The MICs were read off after 2–4 days when the preparation-free controls had become cloudy as a result of growth. The MIC is defined as the lowest preparation concentration which completely inhibits macroscopically visible growth.

| MIC: Mycobacterium smegmatis | | |
|---|---|---|
| Microorganism: Ex. No. | DSM 43061 | DSM 43465 |
| 10 | 4 | 4 |
| 11 | 8 | 4 |
| 12 | 4 | 4 |
| 13 | 8 | 8 |
| Isoniazide | 4 | 1 |
| Streptomycin | 4 | 4 |

The compounds of the general formulae (I), (Ia), (Ib), (Ic), (Id) and (Ie) according to the invention have a broad antibacterial spectrum combined with low toxicity especially against gram-positive bacteria, Haemophilus influenzae, anaerobic microorganisms and rapidly growing mycobacteria. These properties make their use as chemotherapeutic active compounds in human and veterinary medicine possible.

The compounds according to the invention are particularly active against bacteria and bacteria-like microorganisms such as mycoplasma. They are therefore particularly highly suitable for the prophylaxis and chemotherapy of local and systemic infections in human and veterinary medicine which are caused by such pathogens.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compound(s) can optionally also be present in microencapsulated form in one or more of the excepients indicated above.

The therapeutically active compounds should be present in the abovementioned pharmaceutical preparations in a concentration of approximately 0.1 to 99.5, preferably of approximately 0.5 to 95%, by weight of the total mixture.

Apart from the compounds according to the invention, the abovementioned pharmaceutical preparations can also contain further pharmaceutical active compounds.

In general, it has proven advantageous both in human and in veterinary medicine to administer the active compounds (s) according to the invention in total amounts of approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts of approximately 1 to approximately 80, in particular 3 to 30, mg/kg of body weight.

For the purpose of widening the spectrum of action and in order to achieve an increase in action, the compounds according to the invention can also be combined with other antibiotics.

Eluent Mixtures Used

I Dichloromethane: methanol

Starting Compounds

EXAMPLE I

2-Methyl-6-nitrooxazolo[4,5-b]pyridin-2(3H)-one

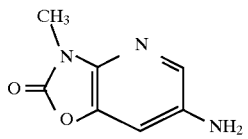

25 g (138 mmol) of 6-nitrooxazolo[4,5-b]pyridin-2(3H)-one (Helv. Chem. Acta 1976, 59, 1593) and 31 ml (207 mmol) of diazabicycloundecene (DBU) in 800 ml of DMF are stirred at 50° C. for 1 h. 86.7 ml (1.38 mmol) of iodomethane are then added dropwise and the reaction mixture is stirred at 100° C. for 16 h. For working up, then DMF is stipped off in vacuo, the residue is treated with dichloromethane and the insoluble produce is filtered off with suction and dried.

Yield: 21.4 g (79% of theory)

$^1$H-NMR (200 MHz, [D$_6$]DMSO): δ=9.0 (d, 1H); 8.54 (d, 1H); 3.40 (s, 3H).

EXAMPLE II

6-Amino-3-methyloxazolo[4,5-b]pyridin-2(3H)-one

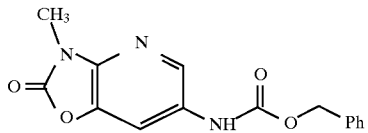

1.56 g (8 mmol) of the compound from Example I and 450 mg of Pd—C (10%) in 100 ml of methanol are stirred under hydrogen (1 atm)) for 6 h. The catalyst is filtered off, the solvent is stripped off and the residue is dried.

Yield: 1.2 g (91% of theory).

$^1$H-NMR (200 MHz, [D$_6$]DMSO): δ=7.50 (d, 1H); 6.98 (d, 1H); 5.20 (bs, 1H); 3.3 (s, 3H).

EXAMPLE III

6-Benzyloxycarbonylamino-3-methloxazolo[4,5-b]pyridin-2(3H)-one

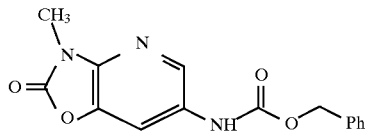

7.1 g (42.9 mmol) of the compound from Example II in 300 ml of THF and 40 ml of satd NaHCO$_3$ solution are treated dropwise at 0° C. with 6.7 ml (47.19 mmol) of benzyl chloroformate. After 1 h, 1 l of water is added and the precipitate is filtered off with suction, washed with water and petroleum ether and dried.

Yield: 12.4 g (96% of theory).

R$_f$ (I, 10:1)=0.66

$^1$H-NMR (200 MHz, [D$_6$]DMSO): δ=9.95 (bs, 1H); 8.10 (d, 1H); 7.80 (d, 1H); 7.30–7.50 (m, 5H); 5.18 (s, 2H); 3.28 (s, 3H).

EXAMPLE IV

6)N-allyl-N-benzyloxycarbonylamino)-3-methyloxazolo[4,5-b]pyridin-2(3H)-one

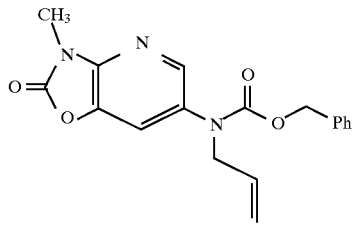

0.7 g (29 mmol) of sodium hydride (80% in paraffin) is added to a solution of 8 g (26.7 mmol) of the compound from Example III in 300 ml of DMF and the reaction mixture is stirred at room temperature for 1 h. It is then treated with 2.5 ml (29 mmol) of allyl bromide and stirred for a further 2 h at room temperature. The mixture is added to 800 ml of water, and the aqueous phase is extracted with diethyl ether and dried (Na$_2$SO$_4$), and the solvents are stripped off in vacuo. The crude product is recrystallized from tert-butyl ethyl ether.

Yield: 7.42 g (82% of theory).

R$_f$ (I, 10:1)=0.30

$^1$H-NMR (200 MHz, [D$_6$]DMSO): δ=8.10 (d, 1H); 7.80 (d, 1H); 7.20–7.45 (m 5H); 5.70–5.95 (m, 1H); 5.00–5.20 (m, 4H); 4.28 (d, 2H); 3.30 (s, 3H).

EXAMPLE V 6-(N-Benzyloxycarbonyl-N-(2,3-dihydroxyprop-1-yl)amino)-3-methyloxazolo[4,5-b]pyridin-2(3H)-one

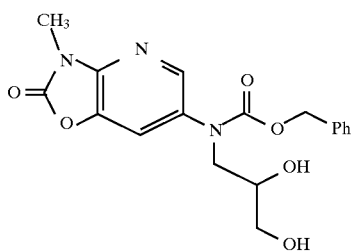

A solution of 7.27 g (21.4 mmol) of the compound from Example IV and 14.9 g (128.2 mmol) of N-methylmorpholine N-oxide in 400 ml of acetone and 100 ml of water is treated with 23.6 ml of a solution of osmium tetroxide (2.5% in water), and the reaction mixture is stirred at room temperature for 16 h. The solution is cooled to 0° C., treated with 240 ml of NaHSO3 solution (39% strength) and stirred at room temperature for a further 2 h. The reaction mixture is treated with water and said NaCl solution (1:1), the aqueous phase is extracted with ethyl acetate and the combined organic phases are dried (Na$_2$SO$_4$). After stripping off the solvents in vacuo, the title compound is obtained as a yellow solid.

Yield: 8.1 g (quant.)

R$_f$ (I, 10:1)=0.32

$^1$H-NMR (200 MHz, [D$_6$]DMSO): δ=8.14 (d, 1H); 7.80 (d, 1H); 7.10–7.45 (m, 5H); 5.10 (bs, 2H); 4.90 (d, 1H); 4.54 (t, 1H); 3.40–3.80 (m, 3H); 3.28 (s, 3H).

EXAMPLE VI

6-Acetylamino-2-methylthiazolo[5,4-b]pyridine

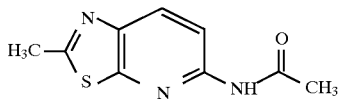

2.85 g (20.2 mmol) of 2,6-diaminothiazolo[5,4-b]pyridine (cf. J. Org. Chem 1973, 38, 4383) in 4.3 ml of acetic anhydride are heated under reflux for 2 h. The reaction mixture is concentrated, and the residue is rendered alkaline using 1M NaOH solution. The mixture is extracted with ethyl acetate and dried (MgSO$_4$) and the solvents are stripped off in vacuo Yield 2.71 g (65% of theory)

R$_f$ (I, 10:1)=0.53

EXAMPLE VII

6-Amino-2-methylthiazolo[5,4-b]pyridine

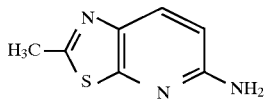

1.33 g (5.96 mmol) of the compound from Example VI in 17.3 ml of concentrated hydrochloric acid are heated under reflux for 1 h. For working up, the reaction mixture is concentrated in vacuo and brought to pH=9 using 1M NaOH solution and extracted with ethyl acetate. The combined organic phases are dried (MgSO$_4$) and the solvent is stripped off in vacuo.

Yield: 0.8 g (81% of theory)
$R_f$ (I, 10:1)=0.58 EXAMPLE VIII
6-Isocyanato-2-methylthiazolo[5,4-]pyridine hydrochloride

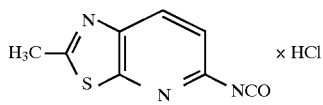

1.01 g (6.1 mmol) of the compound from Example VII and 810 μl (6.71 mmol) of trichloromethyl chloroformate in 10 ml of dichloroethane are heated under reflux for 16 h. The mixture is allowed to cool to room temperature, and the resulting precipitate is filtered off with suction, washed with dichloromethane and dried in a high vacuum.

Yield 1.07 g (77% of theory).

PREPARATION EXAMPLES

EXAMPLE 1

5-Hydroxymethyl-3-(3-methyloxazolo[4,5-]pyridine-2-(3H)-one-6-yl)oxazolidin-2-one

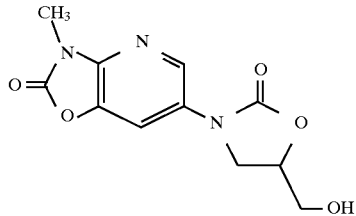

7.75 g (20.8 mmol) of the compound from Example V and 5.8 g (42 mmol) of potassium carbonate in 500 ml of acetonitrile are heated under reflux for 15 h. For working up, the reaction mixture is poured into water and the aqueous phase is saturated with sodium chloride and retracted with ethyl acetate. The combined organic phases are dried ($Na_2SO_4$), the solvents are stripped off in vacuo and the residue is crystallized using diethyl ether.

Yield 3.14 g (57% of theory)
$R_f$ (I, 10:1)=0.83
MS (CI): m/z=283 (M+$NH_4^+$)
$^1$H-NMR (200 MHz, [$D_6$]DMSO): δ=8.20 (d, 1H); 8.02 (d, 1H); 5.22 (t, 1, OH): 4.75 (m, 1H); 4.10 (t, 1H); 3.85 (dd, 1H); 3.49–3.76 (m, 2H), 3.30 (s, 3H).

EXAMPLE 2

(5R)-5-Butyoxymethyl-3-(2-methyliazolo[5,4]-pyridine-2-yl)oxazolidin-2-one

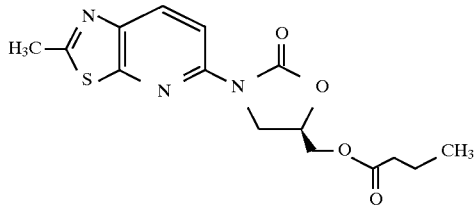

A suspension of 29.0 mg (0.33 mmol) of lithium bromide and 72.0 mg (0.33 mmol) of tributylphosphine oxide in 10 ml of xylene is heated under reflux on a water separator for 1 h. 776 μl (5.6 mmol) of triethylamine and 782 μl (5.6 mmol) of glycidyl butyrate are then added at boiling heat, followed by 1.27 g (5.6 mmol) of the compound from Example VII, and the mixture is stirred under reflux for a further 3 h. It is allowed to cool to room temperature, the solvents are stripped off in vacuo and the residue is purified by chromatography (silica gel, eluent dichloromethane/methanol 30:1)

Yield: 464 mg (25% of theory)
$R_f$ (I, 10.1)=0.9
MS (CI): m/z=336 (M+H)$^+$
$^1$H-NMR (200 MHz, [$D_6$]DMSO); δ=8.33 (d, 1H); 8.22 (d, 1H); 4.98 (m, 1H); 4.35 (m, 3H), 4.12 (dd, 1H); 2.80 (s, 3H); 2.28 (t, 2H), 1.50 (sextet, 2H); 0.80 (t, 3H). cl

EXAMPLE 3

($^4$R)5-Hydroxymethyl-3-(2-methylthiazolo[5,4-b]pyridine-6yl-oxazolidin-2-one

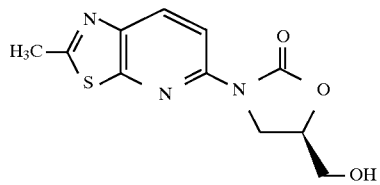

424 mg (1.26 mmol) of the compound from Example 2 in 30 ml of methanol are treated with 35 mg (0.1 mmol) of magnesium carbonate and stirred at room temperature for 3 h. The reaction mixture is treated with ethyl acetate, washed with said $NH_4Cl$ solution and water, dried ($MgSO_4$) and the solvent is stripped of in vacuo.

Yield: 245 mg (75% of theory)
$R_f$ (I, 30:1)=0.43
MS (CI):m/z=266 (M+H)$^+$
$^1$H-NMR (200 MHz, [$D_6$]DMSO); δ=8.33 (d, 1H); 8.25 (d, 1H); 5.23 (t, 1H); 4.75 (m, 1H); 4.25 (t, 1H); 4.05 (dd, 1H); 3.65 (m, 2H); 2.80 (s, 3H).

EXAMPLE 4

5)Methanesulphonyloxy-3-(3-methylthiazolo[4,5]pyridine-2(3H)-one-6yl)oxazolidin -2-one

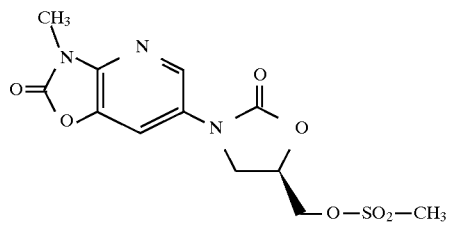

A mixture of 3.0 g (113 mmol) of the compound from Example 1 and 2.7 ml (19.2 mmol) of triethylamine in 120 ml of THF is treated at 0° C. with 1.4 ml (18.1 mmol) of methanesulphonyl chloride and stirred at 0° C. for 1 h. The reaction mixture is added to 1.2 l of ice water and the resulting precipitate is filtered off, washed with water and petroleum ether and dried over $P_2O_5$ in a high vacuum.

Yield: 3.1 g (80% of theory)
$R_f$ (I, 10:1)=0.58
$^1$H-NMR (200 MHz, [$D_6$]DMSO); δ=8.22 (d, 1H); 8.02 (d, 1H); 5.05 (m, 1H); 4.45–4.60 (m, 2H); 4.23 (t, 1H); 3.70 (dd, 1H); 3.30 (s, 3H); 3.32 (s, 3H).

The compound shown in Table 1 is prepared in analogy to the procedure of Example 4.

TABLE 1

| Ex. No. | Compound | Yield (% of theory) | $R_f$ | MS (CI) m/z (M + H)+ |
|---|---|---|---|---|
| 5 | 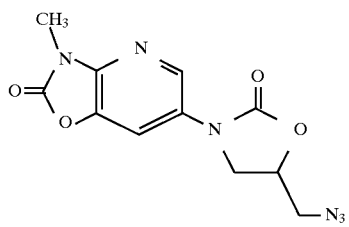 | 90 | 0.5 (I, 20:1) | 344 |

EXAMPLE 6

5-Azidomethyl-3-(3-methyloxazolo[4,5-b]pyridine-2-3H)-one-6-yl)oxazolidin-2-one

A solution of 2.95 g (8.6 mmol) of the compound from Example 4 and and 0.62 g (9.5 mmol) of sodium azide in 150 ml of DMF is stirred at 90° C. for 3 h. The mixture is allowed to cool to room temperature, the DMF is stripped off in vacuo, the residue is treated with water and ethyl acetate and the organic phase is extracted with ethyl acetate. The combined organic phases are dried ($Na_2SO_4$) and the solvent is tripped off in vacuo.

Yield: 2.2 g (88% of theory)

$R_f$ (I, 20:1)=0.55

$^1$H-NMR (200 MHz, [$D_6$]DMSO): δ=8.25 (d, 1H); 8.05 (d, 1H); 4.92 (m, 1H); 4.15 (t, 1H); 3.32 (dd, 1H); 3.15–3.30 (m, 2H); 3.30 (s, 3H).

The compound shown in Table 2 is prepared in analogy to the procedure of Example 6.

TABLE 2

| Ex. No. | Compound | Yield (% of theory) | $R_f$ | MS (CI) m/z (M + H)+ |
|---|---|---|---|---|
| 7 | 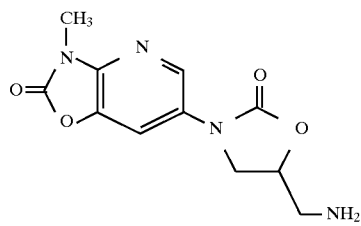 | 96 | 0.71 | 291 |

EXAMPLE 8

5-Aminomethyl-3-(3-methyloxazolo[4,5-b]pyridine-2(3H)-one-6yl)oxazolidin-2-one 2.15 g (7.4 mmol) of the compound from Example 6 and 200 ml of Pd-C (10%) are stirred under hydrogen (1 atm) for 1 h in 50 ml of THF and 50 ml of methanol. After reaction has ended, the catalyst is filtered off, the solvents are stripped off and the residue is dried in a high vacuum.

Yield: 1.96 g (quant.)

$R_f$ (I, 5:1)=0.17

MS (CI): m/z=282 (M+$NH_4^+$)

¹H-NMR (200 MHz, [D₆]DMSO); δ=8.21 (d, 1H); 8.06 (d, 1H); 4.63 (m, 1H); 4.09 (t, 1H); 3.90 (dd, 1H); 3.32 (s, 3H); 3.30–3.45 (bs, 2H).

EXAMPLE 9

(5S)-5-Aminomethyl-3-(2-methylthiazolo[4,5-b]pyridine-2yl-oxazolidin-2-one hydrochloride

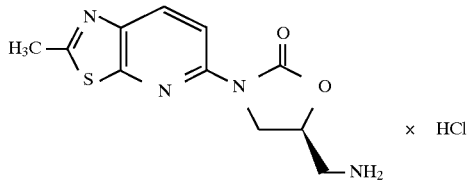

A solution of 210 mg (0.72 mmol) of the compound from Example 7 in 5 ml of dimethoxyethane (DME) is treated dropwise at 50° C. with 0.1 ml (0.84 mmol) of trimethyl phosphite and stirred at 50° C. for a further 3 h 0.1 ml (0.84 mmol) of trimethyl phosphite is again added, and the reaction mixture is stirred for a further 0.5 h, treated with 0.4 ml (2.5 mmol) of 6N HCl and stirred for a further 2 h at 60° C. It is allowed to cool to room temperature and treated with ethyl acetate and said NaHCO₃ solution, the aqueous phase is extracted with ethyl acetate, the combined organic phases are dried (MgSO₄) and the solvents are stripped off in vacuo. The residue is taken up in diethyl ether and treated with an excess of 1M ethereal HCl. The precipitate is filtered off with suction, washed with diethyl ether and dried.

Yield: 105 mg (49% of theory)

¹H-NMR (200 MHz, [D₆]DMSO): δ=8.32 (d, 1H); 8.23 (d, 1H); 4.97 (m, 1H); 4.36 (t, 1H); 4.03 (dd, 1H); 3.25 (m, 2H); 2.80 (s, 3H).

EXAMPLE 10

5-Acetylaminomethyl-3-(3-methyloxazolo[4,5-b]-pyridin-2(3H)-on-6yl)oxazolidin-2-one

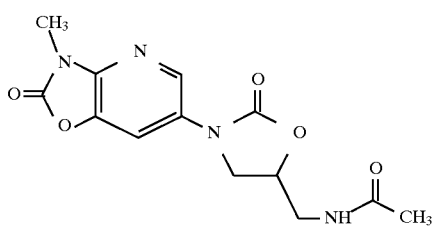

61 μl (0.86 mmol) of acetyl chloride are added at 0° C. to a solution of 150 mg (0.57 mmol) of the compound from Example 9 and 126 ml (0.91 mmol) of triethylamine in 10 ml of dichloromethane and stirred at 0° C. for a further 1 h. The reaction mixture is added to 110 ml of ice water, the aqueous phase is extracted with dichloromethane, the combined organic phases are washed with said NaCl solution and dried (Na₂SO₄), and the solvent is stripped off in vacuo. The residue is crystallized using a little dichloromethane.

Yield: 46 mg (27% of theory)

R$_f$ (I, 20:1)=0.16

MS (CI): m/z=324 (M+NH₄⁺)

¹H-NMR (200 MHz, [D₆]DMSO); δ=8.21 (bt, 1H, NH); 8.15 (d, 1H); 8.02 (d, 1H); 4.74 (m, 1H); 4.15 (t, 1H); 3.73 (dd, 1H); 3.33 (s, 3H); 1.82 (s, 3H).

The compounds shown in Table 3 are prepared in analogy to the procedure of Example 10:

TABLE 3

| Ex. No. | A | R¹¹ | Configuration at C-5 | Yield (% of theory) | R$_f$ (Eluents, ratio) | MS (CI) m/z (M + H)⁺ |
|---|---|---|---|---|---|---|
| 11 | 3-methyl-oxazolo[4,5-b]pyridin-2(3H)-on-6-yl | C(O)-cyclopropyl | R,S | 61 | 0.31 (I, 10:1) | 333 |
| 12 | 3-methyl-oxazolo[4,5-b]pyridin-2(3H)-on-6-yl | C(O)CH₂CH₃ | R,S | 57 | 0.29 (I, 10:1) | 321 |
| 13 | 3-methyl-oxazolo[4,5-b]pyridin-2(3H)-on-6-yl | C(O)OCH₃ | R,S | 23 | 0.44 (I, 10:1) | 323 |

TABLE 3-continued

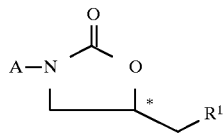

| Ex. No. | A | R[11] | Configuration at C-5 | Yield (% of theory) | R_f (Eluents, ratio) | MS (CI) m/z (M + H)+ |
|---|---|---|---|---|---|---|
| 14 | H₃C—[thiazolopyridine] | —C(O)CH₃ | S | 49 | 0.25 (I, 10:1) | 307 |

We claim:

1. Compounds of the formula (I)

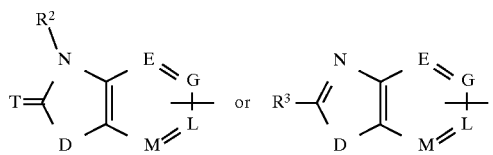

in which

A represents a radical of the formula $$\begin{array}{c} R^2 \\ \diagdown N \\ T=\diagup \diagdown_D \end{array} \begin{array}{c} E\diagdown G \\ \mid \\ M\diagup L \end{array} \quad \text{or} \quad R^3-\begin{array}{c} N \\ \diagup \diagdown_D \end{array} \begin{array}{c} E\diagdown G \\ \mid \\ M\diagup L \end{array}$$

in which

E, G, L and M are identical or different and at least one of the substituents denotes a nitrogen atom and the others denote the radical of the formula —CR⁴, in which R⁴ represents hydrogen, methyl or halogen, R² represents hydrogen, cycloalkyl or cycloalkylcarboyl each having 3 to 8 carbon atoms, or straight-chain or branched alkyl having up to 8 carbon atoms, which is optionally substituted by hydroxyl, halogen, by straight-chain or branched alkoxy, alkoxycarbonyl or alkylthio each having up to 6 carbon atoms or by a radical of the formula —NR⁶R⁷, in which R⁶ and R⁷ are identical or different and denote hydrogen, cycloalkyl, phenyl or straight-chain or branched alkyl having up to 4 carbon atoms, R³ denotes straight-chain or branched alkyl or thioalkyl each having up to 8 carbon atoms, D denotes an oxygen or sulphur atom or a group of the formula —NR⁵, in which R⁵ has the meaning of R² indicated above and is identical to or different from this, T denotes an oxygen or sulphur atom, R¹ represents azido, hydroxyl or a group of the formula —OR⁸, O—SO₂R⁹ or —NR¹⁰R¹¹, in which R⁸ denotes straight-chain or branched acyl having up to 8 carbon atoms or a hydroxyl protective group selected from the group consisting of trimethylsilyl, triisopropylsilyl, tert-butyl-dimethylsilyl, benzyl, benzyloxycarbonyl, 2-nitrobenzyl, 4-nitrogenzyl, tert-butoxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, 2-(trimethylsilyl)ethoxymethyl, benzoyl, 4-methylbenzoyl, 4-nitrobenzoyl, 4-fluorobenzoyl, 4-chlorobenzoyl and 4-methoxybenzoyl, R⁹ denotes straight-chain or branched alkyl having up to 4 carbon atoms or phenyl which is optionally substituted by straight-chain or branched alkyl having up to 4 carbon atoms, R¹⁰ and R¹¹ are identical or different and denote cycloalkyl having 3 to 6 carbon atoms, hydrogen, phenyl or straight-chain or branched alkyl or alkoxy each having up to 8 carbon atoms or an amino protective group selected from the group consisting of benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrogenzoyl, phthalimido, isovaleroyl, benzyloxymethylene, 4-nitrobenzyl, 2,4-dinitrobenzyl, 4-nitrophenyl, 4-methoxyphenyl and triphenylmethyl, or R¹⁰ or R¹¹ denotes a group of the formula —CO—R¹², —CS—R¹²', P(O)(OR¹³)(OR¹⁴) or —SO₂—R¹⁵, in which R¹² and R¹²' are identical or different and denote hydrogen, cycloalkyl having 3 to 6 carbon atoms, trichloromethyl, straight-chain or branched alkoxy having up to 8 carbon atoms, phenyl, benzyloxy or hydrogen, or denote straight-chain or branched alkyl having up to 8 carbon atoms, which is generally substituted by cyano, halogen or trifluoromethyl, or denote straight-chain or branched thioalkyl or acyl each having up to 6 carbon atoms, or denote a group of the formula —NR$^{16}$R$^{17}$,
in which
R$^{16}$ and R$^{17}$ are identical or different and denote hydrogen or straight-chain or branched alkyl having up to 6 carbon atoms,
or
denote a 5-membered aromatic heterocycle having up to 3 heteroatoms selected from the group consisting of S, N and O,
R$^{13}$ and R$^{14}$ are identical or different and denote hydrogen or straight-chain or branched alkyl having up to 4 carbon atoms,
R$^{15}$ denotes straight-chain or branched alkyl having up to 4 carbon atoms or phenyl,
as pure stereoisomers or as stereoisomer mixtures, and their salts.

2. Compounds of the formula (I) according to claim 1, in which
A represents a radical of the formula

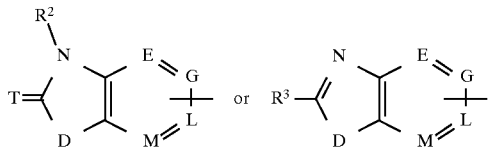

in which
E, G, L and M are identical or different and at least one of the substituents denotes a nitrogen atom and the others denote the radical of the formula —CR$^4$,
in which
R$^4$ denotes hydrogen, fluorine, chlorine or bromine,
R$^2$ denotes hydrogen, cyclopropyl, cyclobutyl, cyclopentyl, cyclohexyl or cycloheptyl, or denotes straight-chain or branched alkyl having up to 6 carbon atoms, which is optionally substituted by hydroxyl, fluorine, chlorine, bromine, by straight-chain or branched alkoxy, alkoxycarbonyl or alkylthio each having up to 4 carbon atoms or by a radical of the formula —NR$^6$R$^7$,
in which
R$^6$ and R$^7$ are identical or different and denote hydrogen, cyclopropyl, cyclobutyl, cyclopentyl, cyclohexyl, phenyl or straight-chain or branched alkyl having up to 3carbon atoms,
R$^3$ denotes straight-chain or branched alkyl or thioalkyl each having up to 6 carbon atoms,
D denotes an oxygen or sulphur atom or a gropu of the formula —NR$^5$;
in which
R$^2$ has the meaning of R$^2$ indicated above and is identical to or different from this,
T denotes an oxygen or sulphur atom,
R$^1$ represents azido, hydroxyl or a group of the formula —OR$^8$, O-SO$_2$-R$^9$ or —NR$^{10}$R$^{11}$,
in which
R$^8$ denotes straight-chain or branched acyl having up to 6 carbon atoms or benzyl,
R$^9$ denotes straight-chain or branched alkyl having up to 3 carbon atoms, phenyl or tolyl,
R$^{10}$ and R$^{11}$ are identical or different and denote cyclopropyl, cyclopentyl, cyclohexyl, hydrogen, phenyl or straight-chain or branched alkyl or alkoxy each having up to 6 carbon atoms, tert-butyloxycarbonyl or benzyloxycarbonyl,
or
R$^{10}$ or R$^{11}$ denotes a group of the formula —CO—R$^{12}$, —CS—R$^{12'}$, P(O)(OR$^{13}$)(OR$^{14}$) or —SO$_2$—R$^{15}$,
in which
R$^{12}$ and R$^{12'}$ are different and denote hydrogen, cyclopropyl, cyclobutyl, cyclopentyl, cyclohexyl, trifluoromethyl or straight-chain or branched alkoxy having up to 6 carbon atoms, phenyl, benzyloxy or hydrogen, or
denote straight-chain or branched alkyl having up to 6 carbon atoms which is optionally substituted by cyano, fluorine, chloride, bromine or trifluoromethyl, or
denote straight-chain or branched thioalkyl or acyl each having up to 5 carbon atoms, or
denote a group of the formula —NR$^{16}$R$^{17}$,
in which
R$^{16}$ and R$^{17}$ are identical or different and denote hydrogen, phenyl or straight-chain or branched alkyl having up to 4 carbon atoms, or
denote isoxazolyl, furyl, thienyl, pyrryl, oxazolyl or imidazolyl,
R$^{13}$ and R$^{14}$ are identical or different and denote hydrogen or straight-chain or branched alkyl having up to 3 carbon atoms,
R$^{15}$ denotes straight-chain or branched alkyl having up to 3 carbon atoms or phenyl,
as pure stereoisomers or as stereoisomer mixtures, and their salts.

3. Compounds of the formula (I) according to claim 1, in which
A represents a radical of the formula

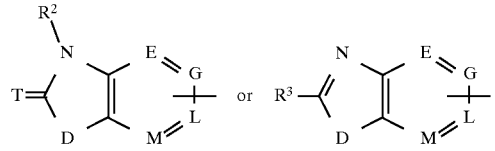

in which
E, G, L and M are identical or different and at least one of the substituents denotes a nitrogen atom and the others denote the radical of the formula —CR$^4$,
in which
R$^4$ denotes hydrogen or fluorine,
R$^2$ denotes hydrogen, cyclopropyl, cyclobutyl, cyclopentyl or cyclohexyl, or denotes straight-chain or branched alkyl having up to 5 carbon atoms, which is optionally substituted by hydroxyl, fluorine, chlorine, bromine, by straight-chain or branched alkoxy, alkoxycarbonyl or alkylthio each having up to 3 carbon atoms or by a radical of the formula —NR$^6$R$^7$,
in which
R$^6$ and R$^7$ are identical or different and denote hydrogen, cyclopropyl, cyclopentyl, cyclohexyl, phenyl or straight-chain or branched alkyl having up to 3 carbon atoms,
R$^3$ denotes straight-chain or branched alkyl or thioalkyl each having up to 5 carbon atoms,
D denotes an oxygen or sulphur atom,
T denotes an oxygen atom,
R$^1$ represents azido, hydroxyl or a group of the formula —OR$^8$, O-SO-$_2$R$^9$ or —NR$^{10}$R$^{11}$.

in which

R[8] denotes straight-chain or branched acyl having up to 5 carbon atoms or benzyl, R[9] denotes methyl, ethyl, phenyl or tolyl, R[10] and R[11] are identical or different and denote cyclopropyl, cyclopentyl, cyclohexyl, hydrogen, phenyl or straight-chain or branched alkyl or alkoxy each having up to 5 carbon atoms, tert-butyloxycarbonyl or benzyloxycarbonyl, or R[10] or R[11] denotes a group of the formula —CO—R[12], —CS—R[12]', P(O)(OR[13])(OR[14]) or —SO$_2$—R[15], in which R[12] and R[12]' are identical or different and denote hydrogen, cyclopropyl, cyclobutyl, cyclopentyl, trifluoromethyl or straight-chain or branched alkoxy having up to 5 carbon atoms, phenyl, benzyloxy or hydrogen, denote straight-chain or branched alkyl having up to 5 carbon atoms, which is optionally substituted by cyano, fluorine, chlorine, bromine, or trifluoromethyl, or denote straight-chain or branched thioalkyl or acyl each having up to 4 carbon atoms; or denote a group of the formula —NR[16]R[17], in which R[16] and R[17] are identical or different and denote hydrogen, phenyl or straight-chain or branched alkyl having up to 3 carbon atoms, or denote isoxazolyl, furyl, oxazolyl or imidazolyl, R[13] and R[14] are identical or different and denote hydrogen, methyl or ethyl, R[15] denotes methyl or phenyl as pure stereoisomers or as stereoisomer mixtures, and their salts.

4. Compounds of the formula (I) according to claim 1, in which the oxazolidinone radical is bonded to the nitrogen-containing ring in position 5 or 6.

5. A method of treating microbial infections to a host in need thereof which comprises administering an effective amount of a compound or salt thereof according to claim 1 to said host.

6. A pharmaceutical composition comprising an effective amount of a compound or salt thereof according to claim 1 and a pharmaceutically suitable excipient.

7. Process for the preparation of the compounds of the formula (I) according to claim 1, said process comprising reacting compounds of the formula (II):

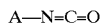    (II)

or compounds of the formula (III):

    (III)

in which, in both formula (II) and (III),

A has the meaning indicated in claim 1, with lithium bromide/(C$_4$H$_9$)$_3$P(O) and epoxides of the formula (IV):

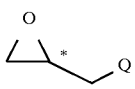    (IV)

in which

Q represents C$_{1-6}$-acyloxy, in an inert solvent and, optionally, in the presence of a base;

and, optionally, if R[1] in the formula (I) represents a hydroxyl function, then the hydroxyl function is liberated by ester hydroxylsis or by a transesterification.

8. The process according to claim 7, which comprises the preparation of compounds of the formula (I) in which R[1] represents a hydroxyl function, said compounds having the formula (Ia):

    (Ia)

in which

A has the meaning indicating in claim 9, and further comprises reaction of the compounds of formula (Ia) with (C$_1$–C$_4$) -alkyl-or phenylsulphonyl chlorides in inert solvents and in the presence of a base to yield the corresponding compounds of the formula (Ib):

    (Ib)

in which

R[9] denotes straight-chain or branched alkyl having up to 4 carbon then reacting the compounds of the formula (Ib) with sodium azide in inert solvents to yield the azides of the formula (Ic):

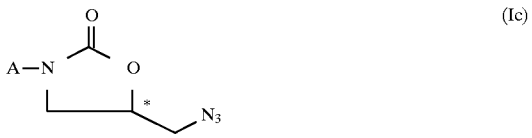    (Ic)

then reacting the compounds of the formula (Ic) with (C$_1$–C$_4$—O)$_3$—P or PPh$_3$ in inert solvents and with acids to yield the amines of the formula (Id):

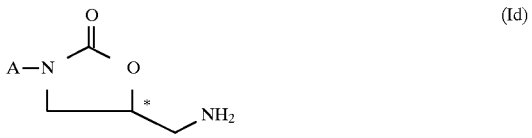    (Id)

then reacting the compounds of formula (Id) with acetic anhydride or other acylating agents of formula (X):

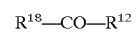    (X)

in which

R[12] denotes hydrogen, cycloalkyl having 3 to 6 carbon atoms, trifluoromethyl, straight-chain or branched alkoxy having up to 8 carbon atoms, phenyl, benzyloxy or hydrogen, or denotes straight-chain or branched alkyl having up to 8 carbon atoms, which is optionally substituted by cyano, halogen or trifluoromethyl, or denotes straight-chain or branched thioalkyl or acyl each having up to 6 carbon atoms, or denotes a group of the formula —$NR^{16}R^{17}$, in which $R^{16}$ and $R^{17}$ are identical or different and denote hydrogen or straight-chain or branched alkyl having up to 16 carbon atoms, or denote a 5-membered aromatic heterocycle having up to 3 heteroatoms selected from the group consisting of S, N and O, and $R^{18}$ represents halogen or the radical —$OCOR^{12}$, in inert solvents to yield the compounds of the general formula (Ie)

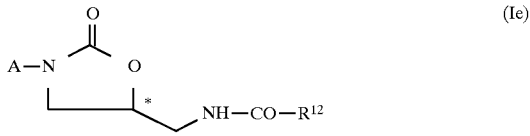

and if $R^1$=$NR^{10}$—$CSR^{12'}$ reacting compounds of the formula (Id) with ethyl dithiocarboxylates and triethylamine and, if $R^1$=$NR^{12}$—CS—$NR^{16}R^{17}$, with thioisocyanates, and optionally converting the compounds into their salts, and, optionally separating stereoisomers.

* * * * *

UNITED STATES PATENT AND TRADEMARK OFFICE
CERTIFICATE OF CORRECTION

PATENT NO : 5,869,659
DATED : February 9, 1999
INVENTOR(S): Stolle, et al.

It is certified that error appears in the above-identified patent and that said Letters Patent is hereby corrected as shown below:

| | |
|---|---|
| Col. 28, line 24 | Delete " 4-nitrogenzyl " and substitute -- 4-nitrobenzyl -- |
| Col. 23, line 58 | Delete " trichloromethyl " and substitute --trifluormethyl--. |
| Col. 28, line 62 | After " which is " delete " generally " and substitute -- optionally -- |
| Col. 29, line 51 | Delete " gropu " and substitute -- group -- |
| Col. 29, line 54 | Delete " $R^2$ " (first occurrence) and substitute -- $R^5$ -- |
| Col. 30, line 7 | After " are " insert -- identical or -- |
| Col. 30, line 14 | Delete " chloride " and substitute -- chlorine -- |
| Col. 31, line 16 | After " $R^{12}$ and " delete " $R^{12}$ " and substitute -- $R^{12'}$ -- |
| Col. 32, line 24 | After " claim " delete " 9 " and substitute -- 7 -- |

UNITED STATES PATENT AND TRADEMARK OFFICE
CERTIFICATE OF CORRECTION

PATENT NO : 5,869,659
DATED : February 9, 1999
INVENTOR(S): Stolle, et al.

It is certified that error appears in the above-identified patent and that said Letters Patent is hereby corrected as shown below:

Col. 32, line 39   After " 4 carbon " insert -- atoms --

Col. 33, line 12   After " upto " delete " 16 " and substitute -- 6 --

Signed and Sealed this

Twenty-eighth Day of September, 1999

Attest:

Attesting Officer

Q. TODD DICKINSON

Acting Commissioner of Patents and Trademarks